US008216778B2

(12) United States Patent
Wang

(10) Patent No.: US 8,216,778 B2
(45) Date of Patent: Jul. 10, 2012

(54) METHODS OF MEASURING CELL VIABILITY IN TISSUE ENGINEERED PRODUCTS

(75) Inventor: Yongzhong Wang, Melrose, MA (US)

(73) Assignee: Genzyme Corporation, Cambridge, MA (US)

(*) Notice: Subject to any disclaimer, the term of this patent is extended or adjusted under 35 U.S.C. 154(b) by 470 days.

(21) Appl. No.: 12/266,246

(22) Filed: Nov. 6, 2008

(65) Prior Publication Data

US 2009/0136981 A1   May 28, 2009

Related U.S. Application Data

(60) Provisional application No. 60/986,751, filed on Nov. 9, 2007.

(51) Int. Cl.
*C12Q 1/00* (2006.01)
*C12Q 1/37* (2006.01)
*C12Q 1/02* (2006.01)

(52) U.S. Cl. .................. 435/4; 435/24; 435/29

(58) Field of Classification Search .................. None
See application file for complete search history.

(56) References Cited

U.S. PATENT DOCUMENTS

| | | | |
|---|---|---|---|
| 4,640,893 A | 2/1987 | Mangel et al. | |
| 4,812,392 A * | 3/1989 | Miyake et al. | ............ 435/3 |
| 5,871,946 A | 2/1999 | Lucas et al. | |
| 6,200,560 B1 * | 3/2001 | Couto et al. | ............ 424/93.2 |
| 6,824,998 B2 | 11/2004 | Davidson et al. | |
| 6,982,152 B2 | 1/2006 | Riss et al. | |
| 6,984,718 B2 | 1/2006 | Zhang et al. | |
| 7,026,111 B2 | 4/2006 | Clausell et al. | |
| 2005/0164321 A1 | 7/2005 | Riss et al. | |

OTHER PUBLICATIONS

Gramer et al. Glycosidase Activities in Chinese Hamster Ovary Cell Lysate and Cell Culture Supernatant; Biotechnology Progress, vol. 9 (1993) pp. 366-373.*
Tannous et al. Codon-Optimized Gaussia Luciferase cDNA for Mammalian Gene Expresion in Culture and In Vivo; Molecular Therapy, vol. 11, No. 3 (2004) pp. 435-443.*
Ghosh et al. Increased Vulnerability of Neuronal Cell Lines to Sodium Nitroprusside-Mediated Toxicity is Caused by Decreased Level of Nitric Oxide Metabolites; Journal of Molecular Neuroscience, vol. 13 (1999) pp. 77-92.*
Promega Technical Bulletin Cytotox-Fluor Cytotoxicity Assay Jun. 2006 downloaded from http://www.promega.com/tbs/tb350/tb350.html.*
International Search Report and Written Opinion dated Feb. 5, 2009 for PCT/US2008/082612.
Breeuwer et al., "Assessment of viability of microorganisms employing fluorescence techniques", Intl. J. Food Microbio., 55:193-200 (2000).
Hug et al., "Rhodamine 110-Linked Amino Acids and Peptides as Substrates to Measure Caspase Activity upon Apoptosis Induction in Intact Cells", Biochemistry, 38:13906-13911 (1999).
Ikada, Y., "Challenges in tissue engineering", J. R. Soc. Interface, 3:589-601 (2006).
Langer et al., "Tissue Engineering", Science, 260:920-926 (1993).
Leytus et al., "Rhodamine-based compounds as fluorogenic substrates for serine proteinases", Biochem. J. 209:299-307 (1983).
Malinin et al., "A Review of Tissue and Organ Viability Assay", Cryobiology, 4(3):104-115 (1967).
Promega Corporation, "CytoTox-Fluor™ Cytotoxicity Assay", Promega Corporation Technical Bulletin, Part# TB350, Promega Corporation, Madison, WI, p. 1-12 (Jun. 2006).
Promega Corporation, "MultiTox-Fluor Multiplex Cytotoxicity Assay", Promega Corporation Technical Bulletin, Part# TB348, Promega Corporation, Madison, WI, p. 1-13 (May 2006).
Steinfeld et al., "Detection of Tripeptidyl Peptidase I Activity in Living Cells by Fluorogenic Substrates", J. Histochem. & Cytochem., 54(9):991-996 (2006).
Vines et al., "Purification and characterisation of a tripeptidyl aminopeptidase I from rat spleen", Biochimica et Biophysica Acta, 1384:233-242 (1998).
Park et al., "Viability Evaluation of Engineered Tissues," *Yonsei Medical Journal*, 41(6): 836-844 (2000).
Da Costa et al., "Comparative analysis of three methods to assess viability of mammalian cells in culture," *Biocell*, 23(1):65-72 (1999).

* cited by examiner

*Primary Examiner* — Rebecca Prouty
*Assistant Examiner* — Paul Martin
(74) *Attorney, Agent, or Firm* — Finnegan, Henderson, Farabow, Garrett & Dunner, LLP

(57) ABSTRACT

This invention provides methods of measuring the viability of cultured cells by detecting one or more cell death-stable proteins or enzyme activities. Methods provided by the invention correlate viability to relative levels of enzyme activity in cell-containing and non-cell-containing fractions of a cell culture.

25 Claims, 8 Drawing Sheets

METHODS OF MEASURING CELL VIABILITY IN TISSUE ENGINEERED PRODUCTS

This application claims the benefit of priority to U.S. Patent Application No. 60/986,751, filed Nov. 9, 2007, the entire contents of which are incorporated herein by reference.

This invention relates to the field of cell biology as well as cell culture and tissue engineering. More specifically, the invention relates to methods of measuring the viability of cultured cells by detecting a protein or enzyme activity.

The field of tissue engineering (reviewed in Langer and Vacanti, *Science,* 260:920-926 (1993)) centers around the use of matrices or scaffolds to support the growth and maintenance of cells. For example, matrix-induced autologous chondrocyte implantation (MACI® implants) is a second-generation autologous chondrocyte implantation (ACI) procedure used to repair catilage. In a MACI® implant, culture-expanded chondrocytes are seeded onto a collagen-based membrane matrix, which later facilitates surgical implantation. MACI® implants may be used to treat cartilage defects arthroscopically or through minimally invasive surgery.

The use of matrices in tissue engineered products presents significant challenges to investigators trying to measure the viability of the engineered products' constituent cells. Existing methods of measuring cell viability rely on at least one of two features of viable cells: the presence of an intact plasma membrane and/or their metabolic activity. In vitro, cell death is accompanied by the loss of plasma membrane integrity. This phenomenon can be readily observed under a microscope using vital dyes. In the most common vital dye assay, the dye trypan blue is added to a suspension of cells. The dye is excluded from viable cells with an intact membrane but stains dead or dying cells with a disrupted membrane. Alternatively, cell viability may be assessed by measuring one or more markers of the cell's metabolic activity. One such approach is to quantify key metabolites (e.g., ATP, NADH), which are present in viable cells but depleted or absent from dead cells. A complementary approach is to assay for specific enzyme activities released from membrane-compromised cells. For example, the Cytox-Fluor cytotoxicity assay (Promega, Madison, Wis., Cat. No. G9260) detects proteases such as tripeptidyl peptidase released from dead cells using the internally quenched fluorogenic peptide substrate bis-(Ala-Ala-Phe)-Rhodamine-110.

When applied to tissue engineered products, most existing cell viability assays require the cells to be isolated (recovered) before assay. The isolation process, however, is often complicated, sometimes harsh, and never 100% efficient. Measurement artifacts may arise as viable cells are lost or killed, or as dead cells are lost, during the procedure. For example, when evaluated by trypan blue exclusion, recovered cells always have a near 100% viability, which fails to reflect the true viability of the original sample from which they were obtained. Attempts to use metabolic activity-based viability assays without first recovering the cells are similarly unsuccessful due to matrix interference, non-specific binding, low upper limit of detection, inadequate range, or poor precision in different media types. Furthermore, existing metabolic activity-based cell viability assays all share a fundamental disadvantage, i.e., the requirement for a positive and/or negative control, with known cell number and viability, in order to measure the viability of the test sample. To make a valid comparison, the cells used in the control and test samples have to be the same type of cells from the same donor or strain, and must also have the same metabolic profile. This approach is not applicable to tissue engineering products where cells, seeded in 3-dimensional matrices, often acquire a very different metabolic profile than the same cells grown in suspension or on a 2-dimensional surface. Additionally, it is often impractical to obtain extra cells and prepare appropriate controls in industrial manufacturing practice where a large number of lots are assayed on a daily basis for viability and quality control.

The viability of the cells being transplanted remains a major determinant in successful treatment with tissue engineered products. In light of the shortcomings of existing viability assays, there is a need for easy, rapid, and accurate methods to measure the viability of cells in tissue engineered products. Such methods must operate over a wide range of cell densities, and with many different cell types, media, and matrices. Furthermore, such cell viability methods advantageously operate without the need for a control cell population.

The present invention provides methods to easily, rapidly, and accurately measure the viability of cells under a variety of conditions and without the need for control cells. The methods are based, in part, on the discovery that the viability of cells in a cultured tissue engineered product can be determined by detecting the fraction of one or more enzyme activities of the cultured cells that are present in the culture's supernatant.

It is theorized, but not relied upon for the purposes of this invention, that upon the loss of membrane integrity which accompanies cell death, the contents of the cell normally bound by the plasma membrane become detectable in the cell culture supernatant. The methods of the invention rely on the detection of a cell death-stable protein or enzyme, i.e., a protein or enzyme which can be detected whether it is present in live or dead cells. The cell viability of the culture can then be determined by detecting the relative amount of the cell death-stable protein or enzyme in the non-cell-containing conditioned medium (e.g. supernatant, or supporting matrix or scaffold) and the cell-containing conditioned medium (e.g. the membrane-intact cells and associated conditioned medium). The amount of cell death-stable protein or enzyme in only the cells of the cell-containing conditioned medium can be determined by disrupting the membrane integrity of membrane-intact cells, e.g., by partial or complete lysis, measuring the total enzyme activity in the cell-containing portion (i.e., disrupted cells and associated conditioned medium) and then subtracting any enzyme activity contributed by the associated conditioned medium. The value that is subtracted is measured by assaying cell-free conditioned medium.

One aspect of the invention provides methods for measuring the fraction of viable cells in a cell population maintained in a culture medium by detecting a cell death-stable protein or enzyme activity in a portion of the conditioned medium not containing cells (e.g. conditioned medium), detecting a cell death-stable protein or enzyme activity in a portion of the medium containing cells (e.g. cells and conditioned medium), and comparing the level of cell death-stable protein or enzyme activity in the two portions. By this method, the fraction of viable cells in the population is proportional to the difference between the level of cell death-stable protein or enzyme activity in the portion containing cells and that of the portion not containing cells.

In some embodiments, the cells assayed may be grown on a traditional two-dimensional cell culture substrate, e.g., glass or tissue culture plastic. In other embodiments, the cells are supported on or in a three-dimensional scaffold or matrix, i.e., the cells are part of a tissue engineered product. In certain embodiments, the cells are grown on a porcine collagen-derived matrix.

In certain embodiments, the methods of the invention further include a step of providing a sample portion of the cell population and a proportional amount of the non-cell containing culture conditioned medium. The sample portion is then divided into a cell-containing (i.e., cells plus conditioned medium) and non-cell-containing (conditioned medium only) fraction and processed according to the methods of the invention.

In certain embodiments, the membrane integrity of the cells of the sample portion is disrupted by, e.g., shearing, sonnication, low barometric pressure, high temperature, low temperature, chemical or enzymatic lysis, or membrane decoupling agents. In some embodiments, the membrane integrity may be disrupted by the addition of an amphiphilic molecule. In certain embodiments, the amphiphile is saponin.

Further aspects of the invention provide methods for measuring the fraction of viable human chondrocytes present in the matrix of a tissue-engineered product having a cell density of between $1.5 \times 10^4$ and $6 \times 10^6$ cells/cm$^2$ maintained in a culture medium. The steps include providing a portion of the tissue engineered product which contains cells and a proportional amount of the culture conditioned medium, providing a portion of the culture conditioned medium not containing cells of the tissue engineered product, adding saponin, and bis-(Ala-Ala-Phe)-Rhodamine-110 to the portions, and detecting fluorescent signals from cleaved bis-(Ala-Ala-Phe)-Rhodamine-110 in the two portions. In some embodiments, Ala-Ala-Phe-AMC, or another substrate with a conjugated leaving group can replace bis-(Ala-Ala-Phe)-Rhodamine-110 in these methods. The fraction of viable cells in the tissue engineered product is proportional to the difference in fluorescent signal strength between the cell-containing and non-cell-containing portions divided by the total amount of the fluorescent signal in both portions.

In another aspect, the invention provides methods of determining the cytotoxicity of a test treatment (e.g., treatment with pharmacological, or biological compounds; or exposure to various conditions, e.g., of osmolarity, pH, temperature, or barometric pressure; or photic, electric or mechanical treatments; or combinations of these) to a test population of cultured cells. The method entails applying the test treatment to the test population, measuring the fraction of viable cells in the test population by the methods of the invention, and comparing the measured viability of the test population to the viability of an untreated population ("control population") of the cultured cells.

The methods of the invention may be used with a variety of cells under a variety of conditions. In some embodiments, the cells may be mammalian (e.g., human, primate, ovine, bovine, porcine, equine, feline, canine, or rodent). In certain embodiments, the cells are human. Cells derived from any source tissue may be used in the methods of the invention. In particular embodiments the cells are chondrocytes.

The methods of the invention may be used with cells at a wide range of densities. In some embodiments the cells are present at a density of between $1.5 \times 10^4$ and $6 \times 10^6$ cells/cm$^2$. In other embodiments, the cells may be present at a density of between $2.2 \times 10^4$ and $2.8 \times 10^6$ cells/cm$^2$, between $3.5 \times 10^4$ and $2.8 \times 10^6$, or between $5 \times 10^4$ and $1 \times 10^6$ cells/cm$^2$. In certain embodiments, the cells may be present at a high density of at least $2.0 \times 10^5$, $5.0 \times 10^5$, $1.0 \times 10^6$, $2.0 \times 10^6$, $2.8 \times 10^6$, $3 \times 10^6$, $4 \times 10^6$, $5 \times 10^6$, $6 \times 10^6$, $8 \times 10^6$, $10 \times 10^6$ cells/cm$^2$, or still higher densities.

In some embodiments of the invention, the cell death-stable enzyme activity is measured by contacting a sample portion with a substrate of the cell death-stable enzyme activity, where the substrate is conjugated to a detectable leaving group, and then detecting the leaving group. By this method, the amount of leaving group detected is proportional to the level of cell death-stable enzyme activity present in the sample portion. In various embodiments, the leaving group may be chromogenic, luminogenic, or fluorogenic. In particular embodiments, the leaving group is fluorescent. In certain embodiments, the leaving group is Rhodamine-110. In other embodiments, the leaving group is a coumarin derivative, e.g., 7-amino-4-methyl coumarin (AMC).

A substrate for an enzyme activity can be any molecule processable by the enzyme. In certain embodiments, the substrate is a tripeptide. In some embodiments, the substrate is bis-(Ala-Ala-Phe)-Rhodamine-110. In other embodiments, the substrate is Ala-Ala-Phe-AMC.

In some embodiments, the methods of the invention may further include the step of adding an agent which modulates (e.g. enhances/increases or attenuates/decreases) the signal of a leaving group. In some embodiments, the agent may modulate the signal by at least 5, 10, 15, 20, 40, 60, or 80%; or more than 1, 2, 3, 5, 10, 50, or 100-fold. In certain embodiments, the agent which modulates the signal of the leaving group, acts by attenuating the signal of the leaving group. In particular embodiments, the agent that attenuates the signal of the leaving group is phenol red. In some embodiments, the phenol red may be present at a concentration of up to 10, 20, 40, 60, 70, 100, 150, 200 mg/L, or more.

In various embodiments of the invention, the cell death-stable enzyme activity detected may be, e.g., anabolic or catabolic, an oxidoreductase, transferase, hydrolase, lyase, kinase, phosphatase, isomerase, or ligase. In some embodiments the cell death-stable enzyme activity may be proteolytic, e.g., one or more tripeptidyl peptidases, chymotrypsin, or chymotrypsin-like enzymes, such as calpain.

In some embodiments, the cell death-stable protein or enzyme activity is a protein or enzyme activity that is stable following either necrotic, programmed cell death, or both (and preferably stable following either form of cell death). In other embodiments, the cell death-stable protein or enzyme activity is a necrotically stable protein or enzyme activity. In still other embodiments, the cell death-stable protein or enzyme activity is a programmed cell death-stable protein or enzyme activity.

In some embodiments, the methods of the invention can include a quality control assay. In such embodiments, the methods of the invention may further include the step of detecting a contaminant-specific enzyme activity in either the cell containing or non-cell-containing portions, or both. Detecting a contaminant-specific enzyme activity is indicative of culture contamination.

The accompanying drawings, which are incorporated in and constitute a part of this specification, illustrate several embodiments of the invention and together with the description, further serve to explain the principles of the invention.

DEFINITIONS

Figure 1:
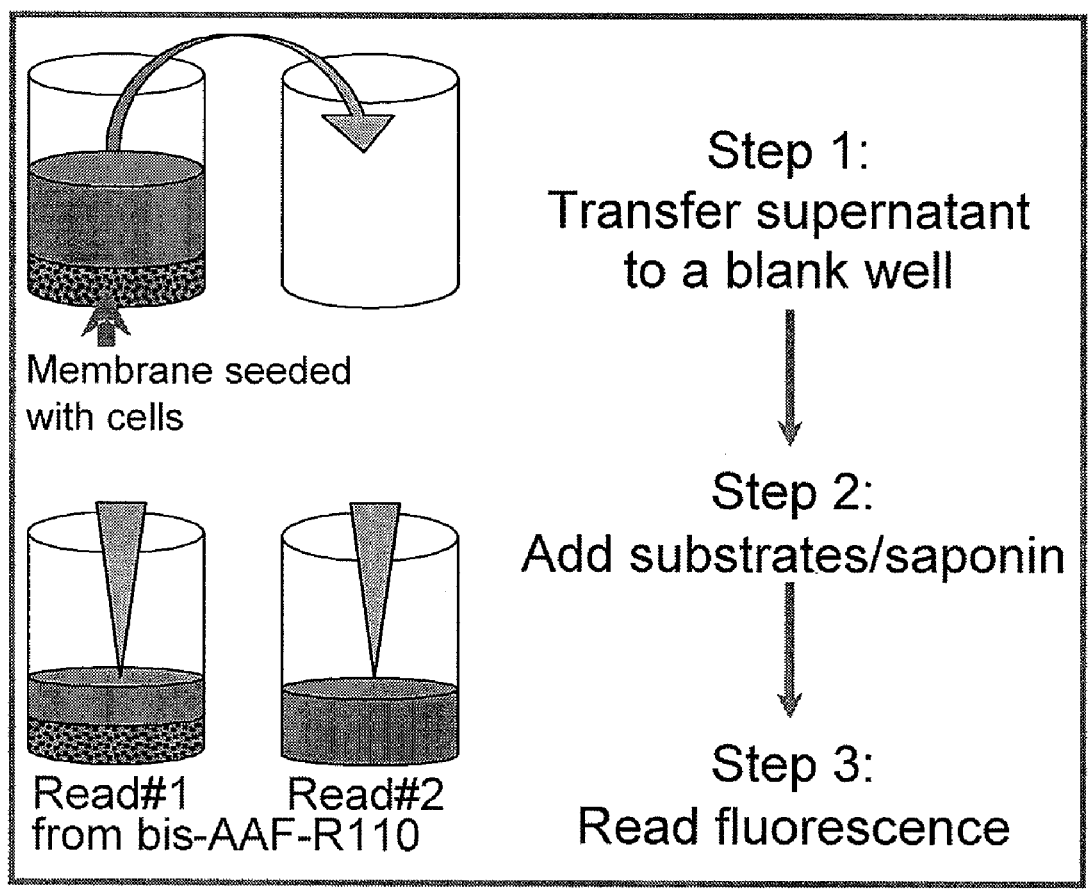
FIG. 1 is a schematic depiction of a cell viability assay.

The singular forms "a," "an," and "the" include plural reference unless the context clearly dictates otherwise.

Unless otherwise indicated, the term "about" means±10%.

"Surface area" as used herein, e.g., square area, $cm^2$, refers to the macroscopic surface area of a substrate, i.e., the Z axis projection of the surface onto the two dimensional plane.

"Density" as used herein, means an average number of some substance, e.g., a cell or other object, per unit area or volume. Most frequently in this application, density will be in the context of a cell density: the number of cells per unit of surface area. This average quantity is approximated by dividing the number of cells seeded by the macroscopic surface area of the surface on which they are grown. This definition contemplates both two-dimensional surfaces, as well as three-dimensional structures or lattices.

The term "medium" as used in this application, refers to all components which support the growth or maintenance of cells in culture. This may include traditional liquid cell culture medium and any additional factors that said medium may contain. These factors may include, for example, serum, antibiotics, growth factors, pharmacological agents, buffers, pH indicators, and the like. Medium shall not generally refer to any matrix or support upon, or within, which the cells are maintained or grown unless clearly indicated otherwise. Accordingly, in a tissue engineered product, the matrix is typically part of the cell-containing portion.

Accordingly, "a portion of the cell culture medium not containing cells" includes a liquid portion of the medium, and not any cell-containing matrix. Similarly, "a portion of the cell culture medium containing cells" includes either isolated cells or matrix-associated cells, in association with medium.

By "conditioned medium" it is meant medium which has been contacted with cells to allow for the composition of the medium to be modified, e.g. by the uptake or release of one or more metabolites, nutrients, or factors, e.g., one or more cell death-stable proteins or enzyme activities. Unless otherwise indicated, conditioned medium generally means medium which has been in contact with a cell population so as to collect cell death-stable protein or enzyme activity from cells with compromised membrane integrity.

As used in this application, "detectable leaving group" refers to a product of an enzymatic reaction that may be used to monitor the progress of an enzymatic reaction.

By "proteome" it is meant the set of all proteins expressed in a group of cells.

"Recombinant" herein refers to non-native biological molecules, e.g., nucleic acids, their transcriptional or translational products, or cells containing any of the above.

By "intrinsic activity" of an enzyme it is meant its $V_{max}$; i.e., the rate of product production when only the enzyme's ability to process substrate is limiting; reaction conditions are otherwise optimized for the enzyme activity.

"Membrane-intact" as used in this application means the ability to exclude the dye trypan blue under standard laboratory conditions.

By "scaling factor" it is meant a numerical constant determined for a particular assay condition.

"Relative measure" in this application refers to expressing a quantity as a function of a reference value; e.g., expressing one value as a fraction of another.

"Absolute measure" in this application means the actual numerical value of some quantity, i.e., not a relative measure.

EXEMPLARY EMBODIMENTS

The invention provides methods to calculate viability based upon the relative measure of a cell death-stable protein or enzyme activity in two fractions of a sample. Unlike vital dye assays, there is no need to recover cells from the matrix. Accordingly, the methods of the invention may eliminate the measurement artifacts associated with prior methods, e.g., losing cells during the process, underestimating or overestimating viability.

Determining Cell Viability

The invention provides methods of measuring the fraction of viable cells in a population maintained in a culture medium. This is done by comparing the amount of a cell death-stable enzyme activity in a portion of the conditioned medium not containing cells to the amount of the cell death-stable protein or enzyme in a portion of the conditioned medium containing cells. In general, the methods of the invention comprise three steps:

(1) a sample is divided into two portions, a cell-containing portion ("X") and a non-cell-containing portion ("Y");

(2) the cells of the cell-containing portion (or a sample taken from the cell-containing portion) are lysed; and (3) the amount of the cell death-stable protein or enzyme in each portion ("X" and "Y") is detected or measured. The skilled artisan can convert these measurements to the fraction of viable cells in the cell population in a variety of ways.

In one example, the conditioned medium is first divided equally into two portions (i.e., halves), a cell-containing portion ("X") and a non-cell containing portion ("Y"). As shown in FIG. 1 and described in Example 1, when the cell-containing portion ("Y") has half of the conditioned medium of the sample, and the remaining half is in the non-cell-containing portion ("X"), then the fractional viability is simply the difference divided by the sum of the activities, i.e., $$\frac{X-Y}{X+Y} = \frac{\text{activity\_from\_live\_cells}}{\text{total\_activity}}.$$

The numerator of this expression is the enzyme activity present in the membrane-intact cells (the amount in the cell-containing portion, i.e. cells and conditioned medium, less the amount present in the conditioned medium alone), while the denominator is the total amount of enzyme activity present in the sample. If the measured enzyme activity present in the cell containing and non-cell-containing portions of the sample are 500 and 50, then the fractional viability is $$\frac{500-50}{500+50} = \frac{450}{550} \approx 0.82.$$

Of course, in the first step of the methods of the invention, the conditioned medium in the sample need not be divided equally between the cell-containing and non-cell containing portions. Where the fraction of the total conditioned medium in the sample is not divided equally between the two portions, the fractional viability is then given by $$\frac{X-cY}{X+Y}$$
$$\text{where } c = \frac{1-f}{f}.$$

In the first expression, c is a scaling factor which adjusts for the volume of conditioned medium in the cell free portion assayed, relative to the volume of conditioned medium in the cell containing portion assayed. This scaling factor is a function of the non-zero, decimal fraction f of the total sample conditioned medium present in portion Y, the sample portion not containing cells. In an illustrative example, a sample of a tissue engineered product is divided into:

(1) a portion X, containing the cells and 25% of the sample conditioned medium; and (2) a portion Y, not containing cells, containing 75% of the sample conditioned medium.

Here, c is $$\frac{1-.75}{.75} = \frac{.25}{.75} = \frac{1}{3}.$$

If the measured enzyme activity is 400 and 30 for X and Y, then $$\text{viability} = \frac{400 - \frac{1}{3}30}{400+30} = \frac{390}{430} \approx 0.91.$$

The foregoing discussion included detailed means to calculate viability using methods provided by the invention. This may be in the context of a culture grown solely for assay, or for the purpose of estimating the viability of some larger population. For example, in a "lot release" assay for a tissue engineered product, the viability of the product's constituent cells are determined by taking a sample of the product (i.e., a biopsy), and some of the overlying conditioned medium. In its simplest form, the percentage of the total conditioned medium overlying the product and the percentage of the product's total surface area or volume (and therefore cells) biopsied, are the same. For example, if a biopsy includes about 2% of the cells of the product, about 2% of the volume of conditioned medium overlying the product should also be present in the sample. Sampling may be done by taking either the cells and conditioned medium together, or in series (in either order), or some combination of the two techniques (e.g., take cells and some conditioned medium, then remove additional conditioned medium) using any number of steps contemplated by the skilled artisan. The equations above implicitly assume this 1:1 percent cell to percent volume ratio in the sample.

The skilled practitioner will appreciate that the 1:1 cell to volume sampling ratio may be varied, and that particular cell types, products, or culture conditions may be amenable to, or even require, altered ratios of cells and conditioned medium in a sample. As would be apparent to the skilled artisan, particular modifications to the calculations presented above should be employed depending on the sampling strategy used. For example, the ratio of percent conditioned medium volume to percent cells in a sample deviates from 1, then the viability of the sample can be given by $$\text{viability} = \frac{X-Y}{X+Y+2Y(\alpha-1)} = \frac{\text{activity\_from\_live\_cells}}{\text{corrected\_total\_activity}}$$

where $\alpha$=the ratio of percent of the total cells to percent of the total conditioned medium volume in the sample. Thus, if a sample includes 2% of the total cells and 4% of the total volume of conditioned medium (i.e., the ratio of the percentage of total cells and percent of conditioned medium is less than 1), and the activity in the "X" and "Y" sample portions are 1000 and 200, respectively, then $$\text{viability} = \frac{1000-200}{1000+200+2\times 200 \times \left(\frac{1}{2}-1\right)} = 0.8$$

Alternatively, the ratio of percent cells to percent conditioned medium volume to in a sample may greater than 1. Thus, if a sample includes 5% of the total cells and 1% of the total conditioned medium, and the activity in the "X" and "Y" sample portions are 820 and 20, respectively, then $$\text{viability} = \frac{820-20}{820+20+2\times 20 \times (5-1)} = 0.8$$

Notably, in these examples, the correction only needed to be made in the denominators of the equations already presented above. This revised equation assumes that the total volume of conditioned medium present in the sample is divided equally between the "X" and "Y" portions assayed. When the conditioned medium is not divided equally, this same denominator correction may be applied to the equation, already provided, for situations where the conditioned medium is not divided equally between the "X" and "Y" portions of a sample.

The methods for determining cell viability provided by the invention eliminate the need for control cells. Control cells are used to calibrate an enzyme-based assay for a particular culture medium, matrix, or cell type. This is, in part, because existing assays make absolute measures of protein or enzyme activity. Absolute measures of protein or enzyme activity can be affected by the presence or absence of, for example, serum, supplements, vitamins, phenol red, or matrix/substrate. In addition, absolute measures of protein or enzyme activity can be affected by intrinsic donor-to-donor, strain-to-strain, and cell passage-to-passage variabilities.

Additionally, existing methods often saturate at even the low end of densities used in applications such as tissue engineering. The methods provided by the invention are useful for measuring viability in high cell density applications, such as tissue engineering.

Cell Death-Stable Protein and Enzyme Activities, Assay Conditions, and Cell Disruption A cell death-stable protein or enzyme activity is one that persists at detectable levels through cell death occurring by various mechanisms, e.g., programmed cell death (an energy-requiring process) or necrosis (a non-energy-requiring process). Because various cell death processes affect different proteins to different extents, a cell death-stable protein may be programmed cell death-stable, necrotically stable, or both. For an overview of cell death, see, e.g., Guimaraes and Linden, *Eur. J. Biochem.*, 271:1638-1650 (2004) and Hengartner, *Nature*, 407:770-6 (2000).

In some embodiments, the relative concentration of the cell death-stable protein or enzyme activity is unaffected, or changes no more than 5, 10, 15, 20, 40, 60, or 80%, or no more than 1, 2, or 3 fold in cells having undergone a cell death process, relative to cells that have not undergone the cell death process. In certain embodiments, the half-life of a cell death-stable protein or enzyme activity may be about 30, 60, 90, or 120 minutes; about 2, 3, 4, 5, 6, 8, 10, or 12 hours; or up to about 1, 2, 3, 4 days, or more.

The skilled artisan will appreciate that proteins or enzyme activities that may be suitable for the present invention can be identified by various means. For example, analysis of the gene expression profile of cells undergoing a cell death process, relative to that of cells not undergoing a cell death process, can be used to identify genes whose protein products are cell death-stable proteins or enzyme activities. Such genes may be differentially expressed no more than 5, 10, 15, 20, 40, 60, or 80%, or no more than 1, 2, or 3 fold in cells undergoing a cell death process, relative to cells that are not undergoing a cell death process. The skilled artisan will recognize that genes identified this way must be further evaluated for the stability of the protein product or enzyme activity under different cell death processes.

Cell death-stable proteins or enzyme activities should be confined by the periphery of the cell, e.g., on or within the plasma membrane, in the cytosol, or within a membrane-bound organelle. Target molecules should not be secreted proteins because the origin of such a protein or enzyme activity, i.e. whether from viable or non-viable cells, cannot be readily determined. The cell death-stable protein or enzyme activity, if confined within the plasma membrane, must become assayable upon loss of membrane integrity.

The membrane integrity of the cells in the cell population may be disrupted by a variety of means known to the skilled artisan. Such means should preserve all or most of the cell death-stable protein or enzyme activity. For example, cell membrane integrity may be disrupted by shearing, sonication, vacuum, high temperature, low temperature (e.g., freezing), chemical or enzymatic lysis, or membrane decoupling agents. Chemical lysis may be achieved by incubation with amphiphilic molecules such as soaps, detergents, or certain glycosides (e.g., saponin). The amount of chemical lysis agent may be adjusted to achieve the desired effect. For example, saponin may be used at a final concentration of between 0.01% and 2% (W/V), e.g., between 0.05% and 0.5%.

The cell death-stable protein or enzyme activity may be either a naturally occurring component of the cell population's proteome, or a non-naturally occurring component, e.g., an expressed recombinant protein(s) or enzyme activity. Such recombinant molecules may be introduced by routine methods known in the art, and may be stably or transiently expressed, i.e., integrated into the genome, or plasmid based. See, e.g., Joseph Sambrook and David Russell, *Molecular Cloning: A Laboratory Manual* Cold Spring Harbor Laboratory Press; 3rd edition (2001).

It will be understood that more than one enzyme may be responsible for a cell death-stable enzyme activity. For example, a group of related enzymes may share a substrate. In some embodiments, an enzyme activity is catalyzed by at least 1, 2, 3, 4, 5, 10, 20, or more, different enzymes.

Detection Methods

A cell death-stable protein can be detected by conventional techniques known in the art, e.g., Western blot, ELISA, mass spectrometry, chromatography, or immunochemistry. Alternatively, a cell death-stable protein can be detected by a characteristic cell death-stable enzyme activity. That is, a protein may be detected indirectly by its function, e.g., a reaction which it catalyzes. Disrupting membrane integrity permits detection of enzyme activity previously inaccessible to molecules in the extracellular milieu by, e.g., diffusion of the enzyme out of the cell, entry of a substrate into the cell, or both.

The skilled artisan will recognize that combinations of substrates and leaving groups can be screened for use in the methods of the invention, without necessarily knowing the enzyme(s) responsible for catalyzing the release of the leaving group. For example, test samples may be made from known quantities of viable and non-viable cells (see, e.g., Example 1) and incubated with a candidate substrate according to the methods of the invention. The leaving group is then detected and its intensity plotted against the known ratio of viable and non-viable cells. Useful substrates will be those that bear a linear correlation with the known proportion of viable and non-viable cells. By testing substrates in this way, it is not necessary to know the source(s) of the cell death-stable enzyme activity.

Enzyme substrate/leaving group conjugates are well known in the art. A useful property of such compounds is the internal quenching of the detectable leaving group. That is, the leaving group is not at all, or only poorly, detectable when conjugated to an enzyme substrate, but rapidly becomes detectable upon dissociation from the substrate, e.g., following enzymatic processing of the enzyme substrate. Classes of leaving groups that may be used in the methods of the invention include, but are not limited to, chromogenic, fluorescent, and luminescent molecules.

Chromogenic molecules for the detection of enzyme activity are well known in the art. Tetrazolium salts and formazans were some of the first substrates used to detect enzymatic activity (Altman, *Prog. Histochem. Cytochem.*, 9:1-56 (1976)). Additional colorimetric compounds may be found in, e.g., U.S. Pat. No. 7,026,111, at column 11.

Luminescent molecules, such as luminol and isoluminol, can be conjugated to enzyme substrates and used directly in the methods of the invention (see, e.g., U.S. Pat. No. 4,748,116). Alternatively, substrates conjugated to luciferin can be employed in a system where luciferase is expressed (see, e.g., U.S. Pat. No. 7,148,030).

The methods of the invention may employ fluorescent leaving groups, e.g., xanthene dyes, fluoresceins, rhodamines, coumarin based molecules, and their derivatives. Available fluorescent molecules are well known in the art. (See, e.g., U.S. Pat. Nos. 4,557,862; 4,640,893; 4,694,070; 4,801,534; 5,352,803; 6,130,101; 6,248,904; 6,342,611; 6,458,966; 6,750,357; 6,759,207; RE38,723, particularly Table II, therein and U.S. patent application Ser. Nos. 10/138,375, filed May 6, 2002 (published as U.S. Patent Publication No. 2003/0208037) and 10/621,311, filed Jul. 18, 2003 (published as U.S. Patent Publication No. 2005/0014160) for examples of fluorescent leaving groups).

The signal produced by the leaving group may be detected by any appropriate means, e.g., visual inspection, a spectrophotometer, luminometer, or fluorometer. In applications where two or more distinguishable leaving groups are present in a sample, they may be detected simultaneously or sequentially.

Substrate-leaving group conjugates useful in the methods of the invention will have a leaving group conjugated to a substrate of a cell death-stable enzyme that is, e.g., a carbohydrate, lipid, protein, peptide, nucleic acid, hormone, or vitamin moiety; or a combination of one or more such substrates. These moieties may be naturally-occurring (e.g., biochemically purified) or synthetic (e.g., chemically synthesized or recombinantly produced). Additionally, these substrates may contain no, some, or all non-native components (e.g. non-natural amino acids, blocking or protecting groups, etc.). Extensive catalogs of enzyme/substrate pairs are known in the art (see, e.g., U.S. Pat. Nos. 4,167,449 (particularly Table II), 5,871,946 (particularly Table I), and 7,026,111 (particularly columns 13-18) for examples of such enzyme/substrate pairs). Additionally, substrate libraries may be generated, as disclosed in U.S. Pat. No. 6,680,178, and screened to identify useful peptide substrates for use in the methods of the invention. In some embodiments, an enzyme activity's substrate preference can be profiled using phage display technology, as disclosed in, e.g., Felber at al., *Biol. Chem.* 386:291-98 (2005).

Other molecules useful in the methods of the invention include conjugates of the fluorescent dye Rhodamine to peptide moieties (Leytus et al., *Biochem. J.,* 209:299-307 (1983)) which are useful in assays for protease activity, e.g., Grant et al., *J. of Biomol. Screen,* 7:531-540 (2002) and Hug et al., *Biochemistry,* 38:13906-11 (1999). These reagents can be integrated into multiplex assays as disclosed in, e.g., U.S. patent application Ser. No. 10/762,836, filed Jan. 22, 2004 (published as U.S. Patent Publication 2005/0164321 on Jul. 28, 2005).

The central role of proteases in maintaining cellular and organismal homeostasis across phyla is one reason for the prevalence of labeled peptide substrates as markers of protease activity (see, e.g., U.S. Pat. Nos. 6,037,137 and 6,984,718, which provide reagents and methods for detecting protease activity in situ and in whole cells).

Intrinsic enzyme activity varies widely among different enzymes and for different substrates of a particular enzyme. Extrinsic factors affecting enzyme activity include the conditions of the medium (e.g., pH, temperature, osmolarity, etc.), the expression level or post-translational regulation of the enzyme, and substrate concentration. Substrate concentration will need to be adjusted by the practitioner appropriately. For a given enzyme, and medium conditions, suitable substrate concentrations may be in the range of, e.g., 0.01 ng/ml to 100 mg/ml, or 10 µg/ml to 10 mg/ml. In some situations, a substrate concentration of between 0.001 mM and 10 mM may be appropriate. Alternatively, the substrate concentration can be between 0.01 mM and 0.5 mM. Similarly, incubation times that allow for the development of detectable signals, will vary widely depending on these same parameters. Accordingly, incubation times may range from 30 seconds or less, up to 1, 2, 3, 5, 10, 20, 30, 45, 60, 75, or 90 minutes; or even 2, 4, 6, 10, or 12 hours, or more.

One useful substrate for the detection of proteolytic activity in the methods of the invention is bis-(Ala-Ala-Phe)-Rhodamine-110 (Promega, Cat. No. G9260). An additional substrate useful in the methods of the invention is Ala-Ala-Phe-AMC (Bachem Cat No. 1-1415.0050). It is theorized, but not relied upon, that the Ala-Ala-Phe tripeptide is a substrate for the extralysosomal tripeptidyl peptidase II enzyme (TPP II; Balow et al., *J. Biol. Chem.,* 261:2409-2417 (1986)) and the lysosomal tripeptidyl peptidase I enzyme (TPP I; Vines and Warburton, *Biochim. Biophys. Acta.,* 1384:233-242 (1998) and Steinfeld et al., *J. Histochem. Cytochem.,* 54:991-996 (2006)). Notably, Ala-Ala-Phe is a common and specific substrate for the bacterial subtilisins (Stambolieva et al., *Arch. Biochem. Biophys.,* 294:703-6 (1992)), which are functionally similar to the tripeptidyl peptidases. Additional substrates of TPP I may be found in, e.g., Tian et al., *J. Biol. Chem.,* 281:6559-72 (2006), which screened large libraries of substrates and U.S. Pat. No. 6,824,998, which disclosed substrates (with precipitating leaving groups) useful for histological applications.

Ala-Ala-Phe is known to also be a substrate for the chymotrypsin enzyme. Other substrates for chymotrypsin and related enzymes, such as calpain, are known in the art—as are structure/function correlations of such enzymes. These are discussed further in, e.g., Sharma et al., *Biol. Chem.* (2008; Aug. 8 electronic publication; PubMed Id (PMID) No. 18690777), Croall and Ersfeld *Genome Biol.* 8:218 (2007); Czapinska and Otlewski *Euro. J. Biochem* 260:571-95 (1999); Perona and Craik *J. Biol. Chem.* 272:29987-90 (1997).

Cell Culture Medium, and Matrix

The invention provides methods which may be used to measure the viability of cultured cells derived from a wide variety of host organisms, e.g., mammals, including humans, and from a wide variety of source tissues. The cells assayed may be derived from tissues in various stages of development. Cells may be derived from an adult, fetal, or embryonic source. The cells may be totipotent or pluripotent stem cells, derived from an organ originating from any of the three primordial germ layers (i.e., ectoderm, mesoderm or endoderm). For example, cells may be derived from skin, heart, skeletal muscle, smooth muscle, kidney, liver, lungs, bone, pancreas, central nervous tissue, peripheral nervous tissue, circulatory tissue, lymphoid tissue, intestine, spleen, thyroid, connective tissue (e.g., chondrocytes), or gonad. The cells may be non-expanded primary cells, culture-expanded primary cells, or established cell lines. Additionally, the cells may be grown in a variety of media, e.g., with or without serum (e.g., chemically defined media), and with or without phenol red.

The invention provides methods to measure the viability of cells over a wide range of cell densities. For example, the cells may be present at a density of between $2.2 \times 10^4$ and $2.8 \times 10^6$ cells/cm², between $3.5 \times 10^4$ and $2.8 \times 10^6$, or between $5 \times 10^4$ and $1 \times 10^6$ cells/cm². The cells may also be present at a high density of at least $2.0 \times 10^5$, $5.0 \times 10^5$, $1.0 \times 10^6$, $2.0 \times 10^6$, $2.8 \times 10^6$, $3 \times 10^6$, $4 \times 10^6$, $5 \times 10^6$, $6 \times 10^6$, $8 \times 10^6$, $10 \times 10^6$ cells/cm², or more. The methods provided by the invention have been practiced with cell densities of up to about $3 \times 10^6$ cells/cm². It is contemplated that the methods would work with cell densities of up $10^6$ cells/cm², or more. It should be understood that all cell densities referenced throughout this disclosure are qualified by the term "average." The skilled artisan will undoubtedly appreciate that local fluctuations in cell density will occur and are contemplated in the methods provided by the invention.

Cells are incubated in medium to allow for the accumulation of cell death-stable protein or enzyme activity in the medium, i.e., to produce conditioned medium. The methods provided by the invention measure viability over the amount of time that the cells are in contact with the medium, i.e., conditioned medium generally cannot be replaced with fresh medium just before assay. Cells may be incubated for a variable amount of time, depending on the particular application, e.g., cell type, cell density, medium type, or half-life of the cell death-stable protein or enzyme activity. Cells may be incubated before assaying for about 1, 5, 10, 30, 60, 90, 120, 150, 180, 210, or 240 minutes; or about 3, 4, 5, 6, 8, 10, 12, 18, or 24 hours; or up to about 1, 2, 3, 4, 5 days, or more.

The methods of the invention are useful to measure the fraction of viable cells grown on a variety of substrates or matrices. Cells may be grown on traditional two-dimensional cell culture substrates, e.g., glass or surface treated plastic. Alternatively, cells can be supported by a scaffold or matrix, e.g., where the cells are part of a tissue engineered product. Suitable scaffolds may include structures composed of metals, plastics, glass, silicon, ceramics, and/or calcium phosphates. Other suitable scaffold materials include absorbable polyesters (e.g. polymers of glycolide or lactide, and derivatives or copolymers thereof); carbohydrate (e.g. hyaluronin, chitin, starch, or alginate); and protein (e.g., collagen (e.g., a porcine collagen-derived matrix) or gelatin), or combinations of any of these matrices. Further discussion of matrices used in tissue engineering may be found in, e.g., Langer and Vacanti (1993); Ikada, *J. R. Soc. Interface*, 3:589-601 (2006); and U.S. Pat. Nos. 6,689,608 and 6,800,296.

Assay Variations

Applicants have discovered that phenol red can further extend the range of cell densities assayable by the methods of the invention. This is achieved by attenuating the signal of the leaving group. That is, phenol red reduces the signal of, e.g., rhodamine-110 (R110), and the assay saturates at a higher cell density. It is theorized, but not relied upon, that deprotonated phenol red exerts this effect because its absorption spectrum has significant overlap with both the excitation and emission spectra of rhodamine 110.

In addition to phenol red for R110, the use of other attenuating agents adapted for use with other leaving groups is also contemplated. Appropriate attenuating agents for particular leaving groups' excitation and or emission spectra will have the desired degree of overlap in its absorption spectrum. Absorption, excitation, and emission spectra are known in the art or may be readily determined empirically, e.g., by fluorometry.

Furthermore, the methods provided by the invention are modular and amenable to multiplexing. That is, additional processes, steps, and/or agents can further extend an assay's utility. For example, the methods provided by the invention may further include the detection of more than one cell death-stable protein or enzyme activity. This is achieved by applying multiple enzyme-specific substrates for two or more cell death-stable enzyme activities in a sample portion using, e.g., orthogonal substrates and/or leaving groups. Such a "detection mixture" contains one or more species of substrate for cell death-stable enzyme activities, coupled to one or more detectable leaving groups. These multiplexing methods can be divided into two broad classes: a single species of leaving group, and multiple species of leaving groups.

A detection mixture where a single species of leaving group is coupled with multiple species of enzyme substrates will produce an integrated signal. That is, the resulting signal is a sum of the detected enzyme activities. For example, each substrate could be processed by a distinct enzyme activity. By assaying and summing over multiple enzyme activities, the integrated signal is a more accurate view of the sample's overall metabolic state. Integrated signals may also be useful where shorter incubation times are desired.

The use of multiple species of leaving groups in the methods of the invention provides independent measures of viability. A detection mixture containing a single species of substrate for an enzyme activity coupled to multiple species of leaving groups provides parallel measures of viability. The different signals offer additional flexibility to investigators using detection equipment which may have machine or detector dependent sensitivities, e.g., at different wavelengths and or intensities.

The use of multiple substrate species, each coupled to a different species of leaving group, offer fully independent measures of viability. The substrates may, e.g., belong to enzymes with low, medium, or high relative activities. The relative activities could vary from low to high by at least 10, 20, 40, or 80%, or by at least 1, 2, 5, 10, 50, 100, 500, or 1000 fold, or more. By making multiple independent measures of viability, an investigator may be more likely to remain in the linear detection range with at least one substrate species.

A further application using multiple leaving groups is a quality control assay. In particular, the methods of the invention may further include the step of adding one or more contaminant-specific substrates, each coupled to the same species of leaving group, and detecting one or more contaminant-specific enzyme activities. The contaminant-specific substrate species are substrates for enzymes specific to common cell culture contaminants such as: fungi, bacteria, archaea, and protists—and absent from the cultured cells' proteomes. Accordingly, detection of the contaminant-specific leaving group indicates contamination of the cultured cell population. Naturally, the leaving group for the contaminant-specific enzyme activities will be distinguishable from the leaving group(s) used to measure the viability of the cultured cells.

The methods of the invention can also be adapted to measure the cytotoxicity of a treatment. A treatment may be an environmental or physiological treatment, e.g., thermal, barometric, mechanical, or photic stimulus. Treatment may also be a chemical treatment, e.g., osmolarity, pH, a pharmacological or biological agent, or any combination of the above. The methods of the invention may further include the steps of applying a treatment to a test cell population, measuring the viability of the test cell population by the methods of the invention and comparing the viability to a control culture of the same cells not exposed to the treatment. In certain embodiments, the cytotoxicity may be calculated as 1 minus the fractional viability of a population. In these embodiments, a control population is not necessary.

EXAMPLES

Example 1

Measuring Cell Viability of a Tissue-Engineered Product

A brief schematic of a cell viability assay is shown in FIG. 1. There, "Read #1" is the amount of cell death-stable or enzyme activity present in the portion of the population containing the cells and conditioned medium, while "Read #2" is the amount of cell death-stable protein of enzyme activity present in the portion of the conditioned medium not containing cells of the culture population.

Human articular chondrocytes were expanded to second or third passage in monolayer cultures. In order to replicate culture conditions used in MACI® implants, chondrocytes were seeded in triplicate onto white opaque 96 well plates on the rough side of ACI-MAIX® membrane matrix punches (6 mm in diameter) at densities of approximately 25,000 to 600,000 cells per punch. Matricel ACI-MAIX® membrane matrix is a porcine collagen based membrane matrix with a smooth side and a rough side. This seeding density is equivalent to $8.75 \times 10^4$ to $2.1 \times 10^6$ cells/cm² which corresponds to $1.75 \times 10^6$ to $42 \times 10^6$ cells per ACI-MAIX® membrane matrix (20 cm²). When the assay is applied to full-sized MACI® implant samples, two small punches (typically 6 mm in diameter) and a proportional amount of conditioned medium are taken from each sample. For two punches 6 mm in diameter, which together represent approximately 2.8% of a 20 cm² membrane, a proportional amount of the conditioned medium is approximately 2.8% of the total volume of the conditioned medium overlying the 20 cm² membrane. In both the full-scale and downscaled cases, blank membrane matrix punches and medium were processed as controls.

Three hours after cell seeding, half of the conditioned medium, which would contain half of the total amount of any proteases released by dead (nonviable) cells, was transferred to empty wells.

Next, a mastermix containing the bis-(Ala-Ala-Phe)-Rhodamine-110 substrate (bis-alanyl-alanyl-phenylalanyl-rhodamine 110; Promega Cat. No. G9260) with saponin (10% w/v aqueous solution, Sigma, St. Louis, Mo., Cat. No. S4521) and phenol red (optional; 0.1% solution prepared by diluting 0.5% phenol red, Sigma Cat. No. P0290, in Phosphate Buffered Saline (PBS)) was added to the samples. Saponin was used to permeate the live cells in the portion containing cells and conditioned medium to make the intracellular proteases accessible to the substrate. The final concentration of various components in the mastermix is typically:

bis-(Ala-Ala-Phe)-Rhodamine-110 substrate, 0.83 mM
Saponin 1.67%
Phenol red 0.167 mg/mL (optional)

After incubation (45-90 min.), the plate was read using a Molecular Devices SPECTRAMAX™ M5 Microplate Reader with the SOFTMAX™ Pro Software at excitation 485 nm-emission 520 nm. The data was then processed in Microsoft EXCEL.

Figure 2:
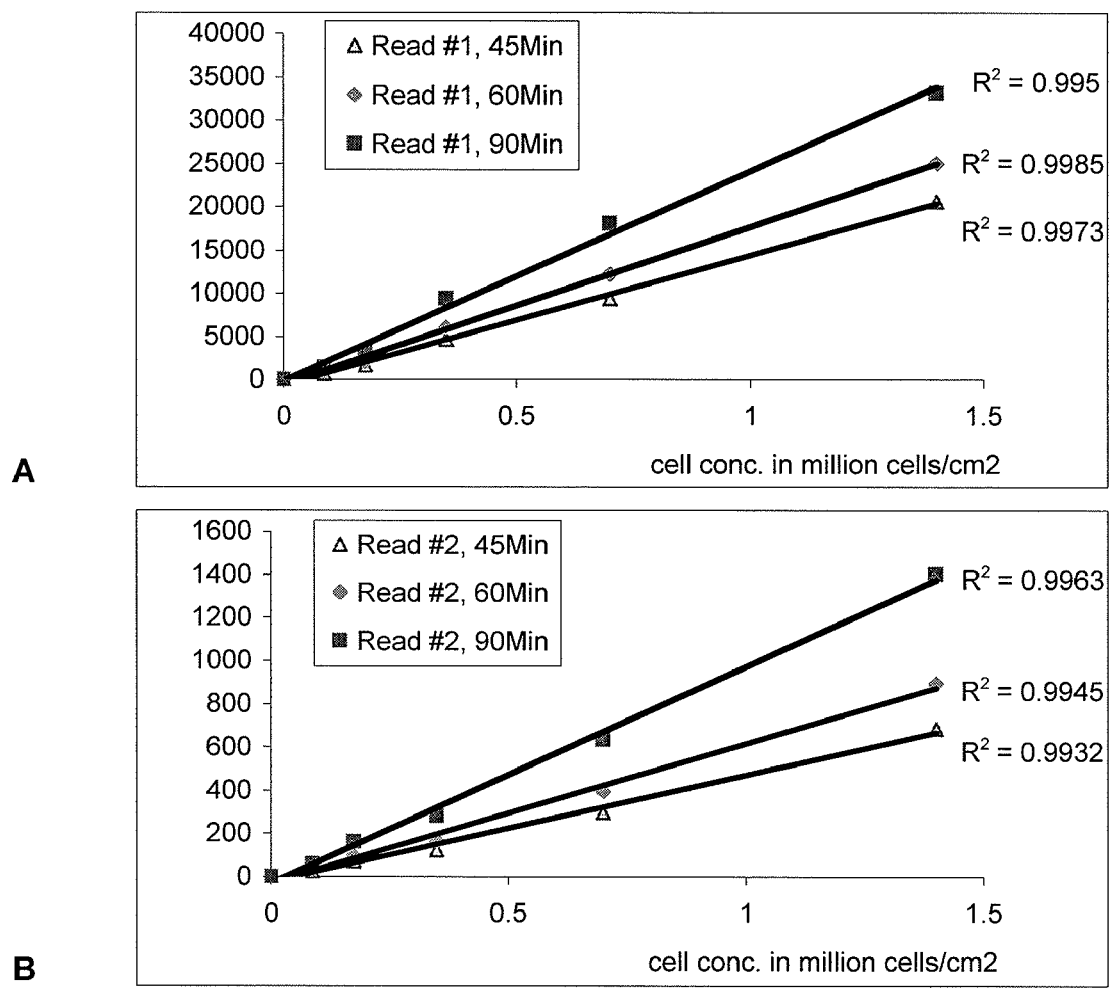
FIG. 2A is a graphical representation of an experiment which demonstrates that the enzyme activity present in the cells and supernatant of a sample is linearly related to the density of the cell population.
FIG. 2B is a graphical representation of an experiment which demonstrates that the enzyme activity present in the supernatant of a sample is linearly related to the density of the cell population.

Results of representative experiments are shown in FIG. 2. Scatterplots of fluorescent reporter signal strength, (Read #1, live cells with supernatant, FIG. 2A; and Read #2, supernatant only, FIG. 2B); as a function of cell seed density are shown. Data points are the average of three replicates. Incubation time with the bis-(Ala-Ala-Phe)-Rhodamine-110 substrate was either 45, 60, or 90 minutes. The relationship between signal and cell density was linear and varied little for all incubation times tested. A 60 minute incubation step was used in subsequent measurements.

Example 2

Assay Accuracy and Precision

Figure 3:
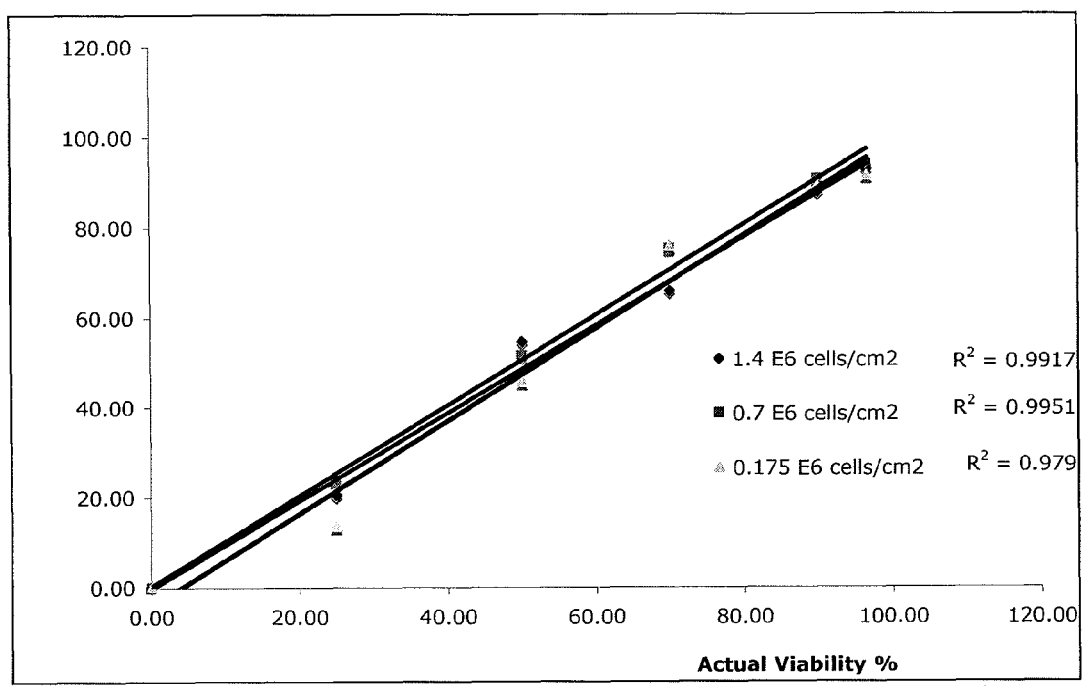
FIG. 3 is a graphical representation of an experiment which demonstrates that the disclosed assay accurately predicts viability.

The accuracy of the assay was evaluated by comparing the measured viability of a culture with a known percentage of viable cells. The culture was composed of a mixture of known quantities of live and dead cells, pre-mixed and seeded at the indicated densities, then processed as in Example 1. The measured viability was plotted as a function of the percent of viable cells in the test mixture (FIG. 3). The plotted data points are the average of two replicates. Typically the difference between the measured viability and the actual viability is less than 15%. For cell seeding densities lower than $0.175 \times 10^6$ cells/cm², a longer incubation time (at least 90 min.) helps ensure assay accuracy.

To measure the inter-strain accuracy of the assay, 1:1 proportions of live and dead cells from 3 different strains were seeded at a density of $7.0 \times 10^5$ cells/cm². Although significant intrinsic variability can exist in the absolute signal levels from different cell strains (Table 1, first data column; % CV=41.49) the variability in measured viability is substantially less (Table 1, second data column; % CV=7.62).

TABLE 1

|  | Read #1 Signal | Measured Viability |
|---|---|---|
| Strain #1 | 20724.01 | 58.27 |
| Strain #2 | 10029.55 | 51.04 |
| Strain #3 | 24999.32 | 51.37 |
| Average | 18584.29 | 53.56 |
| Standard Deviation(SD) | 7710.85 | 4.08 |
| % CV = (100 × SD/Average) | 41.49 | 7.62 |

Example 3

Contribution of Matrix, Reagent, and Analyst Variability to Assay Precision

In order to assess the effect of different analysts and different matrix or reagent lots on the precision of measured viability, cells from a single parent culture were seeded at a density of $7.0 \times 10^5$ cells/cm² on membrane punches and processed as described in Example 1. Three variables were analyzed: matrix lot, assay lot, and analyst. Each variable was tested in two groups—each treatment group having three statistical replicates. The results are shown in Table 2. These results suggest that the assay is relatively insensitive to changes in these technical variables.

TABLE 2

|  | Membrane Matrix | | Assay Reagent | | Analyst | |
|---|---|---|---|---|---|---|
|  | Lot #1 | Lot #2 | Lot #1 | Lot #2 | Analyst #1 | Analyst #2 |
| Run #1 | 78.6 | 80.7 | 75.8 | 79.3 | 75.9 | 77.0 |
| Run #2 | 78.3 | 82.5 | 80.5 | 78.6 | 82.8 | 78.6 |
| Run #3 | 77.6 | 81.6 | 76.1 | 80.7 | 78.4 | 73.7 |
| Average | 78.2 | 81.6 | 77.5 | 79.5 | 79.0 | 76.4 |
| Standard Deviation | 0.5 | 0.9 | 2.6 | 1.1 | 3.5 | 2.5 |
| % CV | 0.7 | 1.1 | 3.4 | 1.3 | 4.4 | 3.3 |

Example 4

Effect of Phenol Red

Figure 4:
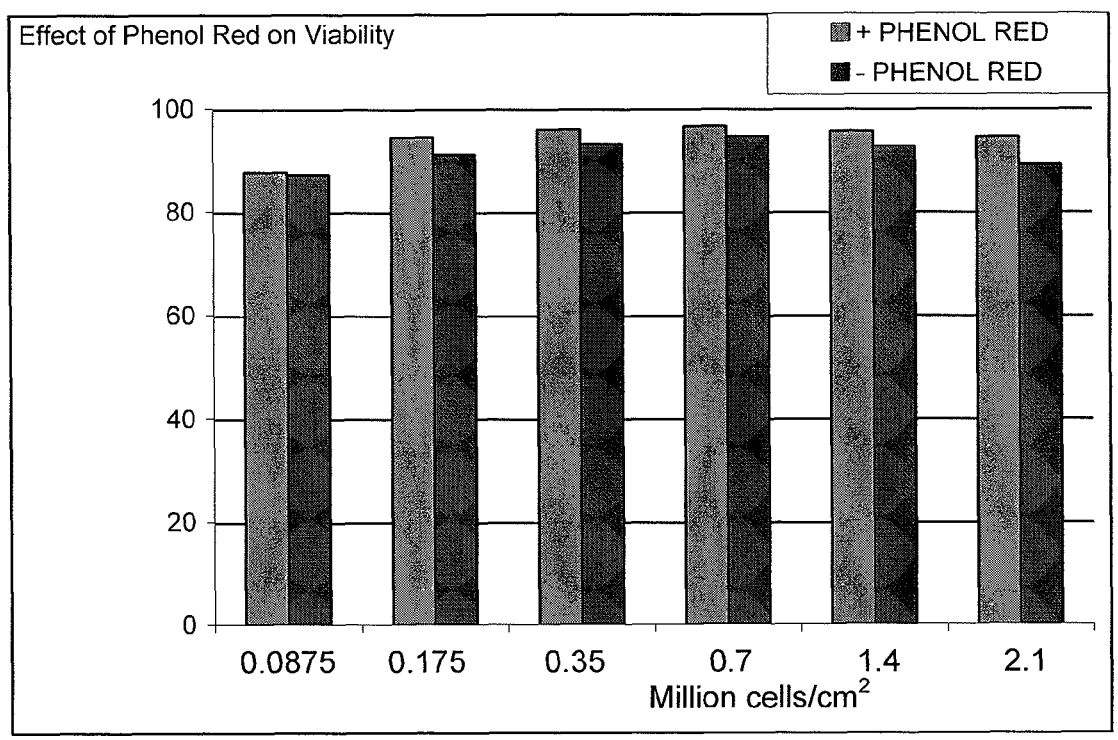
FIG. 4 is a graphical representation of an experiment which demonstrates that the addition of phenol red does not affect the accuracy of the disclosed assay.

During the development of this assay, it was found that the addition of phenol red to the assay mixture could attenuate the signal intensity in a dose-dependent manner, and extend the linear range of the assay to higher cell densities. Cells were seeded at varying densities and processed as in Example 1, with or without phenol red and the average viability of three replicates is shown in FIG. 4. The addition of phenol red does not affect the accuracy of the assay, it merely serves to prevent the signal levels from approaching saturation by suppressing the signal outputs in a dose-dependent manner. The amount of phenol red can be adjusted as needed. Phenol red is not typically needed for seeding densities lower than $0.5 \times 10^6$ cells/cm² membrane matrix.

Example 5

Timing of Phenol Red Addition

The timing of addition of phenol red to the assay mixture was found to be flexible. To demonstrate this, cells from a single strain were sonicated to release all intracellular proteases and seeded at a density of $1.0 \times 10^4$ cells/well in a 96 well plate, in a volume of 100 μl/well. Substrates and phenol red were added in the amount and at the time according to Table 3. The results are shown as the average signal intensity of three replicates per treatment in Table 4. These results demonstrate that phenol red of varying concentrations added at varying time points during the assay is similarly effective in attenuating the signals.

Figure 5:
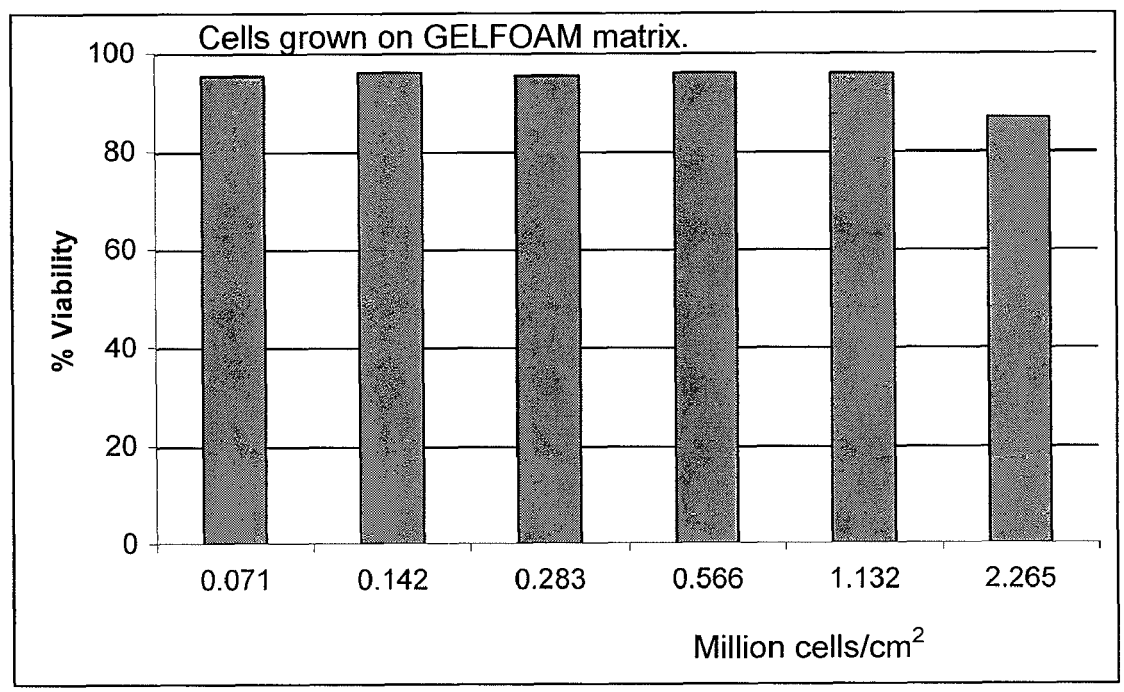
FIG. 5 is a graphical representation of an experiment which demonstrates that the accuracy of the disclosed assay is unaffected by use of an alternative matrix.

The use of phenol red significantly expanded the dynamic range of the new assay to measure viability when using either: a high cell seeding density (typically over $1.4 \times 10^6$ cells/cm$^2$), or in a variety of media including serum containing or serum free, and phenol red containing or phenol red free.

sponge, at densities ranging from $7.1 \times 10^4$ to $2.3 \times 10^6$ cells/cm$^2$. Cells were processed as in Example 1. Results are shown in FIG. 5 as the average viability of three replicates. The viability of the cells, as determined by trypan blue exclusion just prior to seeding, was 91%. These data indicate that the assay is amenable to analyzing cells seeded on a variety of different matrices.

Example 7

Cells Grown on 2D Cultures (Tissue Culture Plastic)

Figure 6:
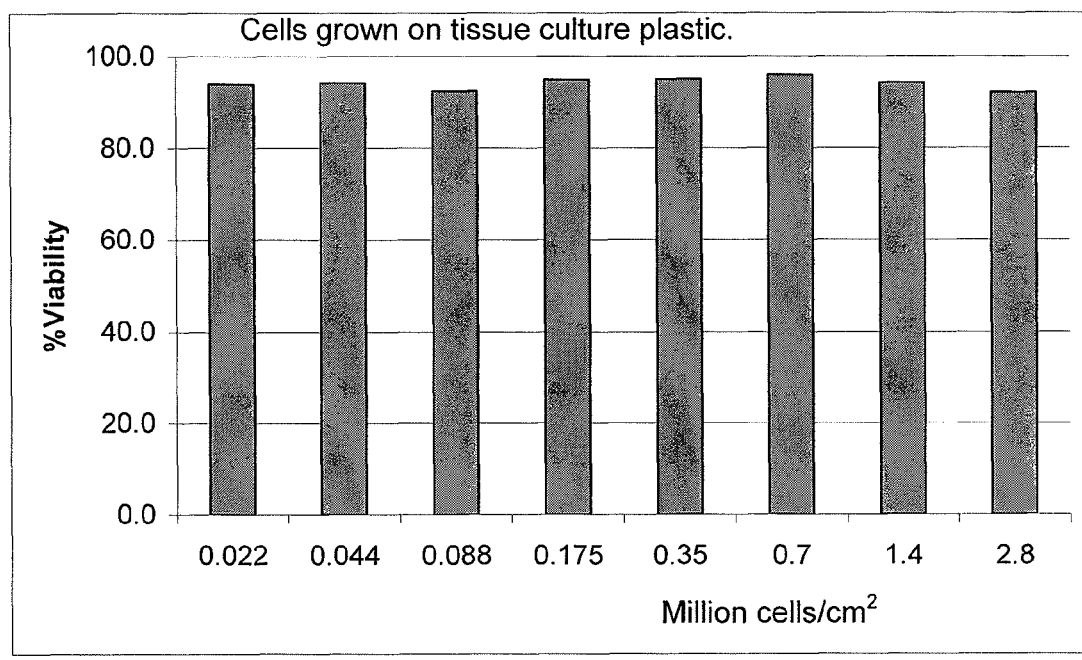
FIG. 6 is a graphical representation of an experiment which demonstrates that the accuracy of the disclosed assay is unaffected by the absence of a matrix.

To demonstrate the effectiveness of the assay in a more traditional tissue culture environment (i.e. growth on an inorganic, flat substrate), cells were seeded directly in a plastic six well tissue culture plate, with no matrix, at densities ranging from $2.2 \times 10^4$ to $2.8 \times 10^6$ cells/cm$^2$. The cells were processed as in Example 1. The results are shown in FIG. 6 as the average viability of two replicates. The viability of the cells, as determined by trypan blue exclusion just prior to seeding, was 96%. These results demonstrate that the assay performs

TABLE 3

| | Group | | | | | | |
|---|---|---|---|---|---|---|---|
| | 1 | 2 | 3 | 4 | 5 | 6 | 7 |
| Time = 0 min (When started), add additional phenol red for the 1st round: | | 2 ul of 0.05% phenol red per well | 2 ul of 0.1% phenol red per well | | | | |
| Time = 30 min: add substrate | | | | | | | |
| Time = 90 min: add additional phenol red for the 2nd round: (60 min after adding substrate) | | | | 2 ul of 0.05% phenol red per well | 2 ul of 0.1% phenol red per well | | |
| Time = 210 min: add additional phenol red for the 3rd round: (180 min after adding substrate) | | | | | | 2 ul of 0.05% phenol red per well | 2 ul of 0.1% phenol red per well |

TABLE 4

| | Group | | | | | | |
|---|---|---|---|---|---|---|---|
| Signals (RFU) at | 1 (no additional phenol red) | 2 | 3 | 4 | 5 | 6 | 7 |
| Time = 60 min (60 min after round 1 additional phenol red and 30 min after addition of substrate) | 336.51 | 155.07 | 104.64 | 264.06 | 288.91 | 310.23 | 326.48 |
| Time = 90 min (Right before round 2 additional phenol red) | 868.22 | 408.44 | 258.21 | 721.74 | 774.08 | 829.01 | 866.34 |
| Time = 90 min (Right after round 2 additional phenol red) | 871.22 | 403.59 | 251.84 | 426.17 | 275.25 | 841.60 | 886.71 |
| Time = 210 min (Right before round 3 additional phenol red) | 3921.60 | 1861.36 | 1170.77 | 1917.11 | 1131.79 | 4039.14 | 4282.18 |
| Time = 210 min (Right after round 2 additional phenol red) | 3550.22 | 1736.73 | 1084.51 | 1777.20 | 1038.75 | 1981.21 | 1313.56 |
| Time = 270 min | 5513.00 | 2522.19 | 1611.28 | 2583.72 | 1561.83 | 2642.22 | 1715.75 |
| Time = 12 hours | 17777.36 | 9809.42 | 6125.19 | 10058.85 | 5868.30 | 9722.61 | 5782.98 |

Example 6

Cells Grown on an Alternative Matrix

To demonstrate the effect of a different matrix material on the method, cells were seeded on GELFOAM™ (Upjohn Pharmacia, Kalamazoo, Mich.), a highly porous gelatin well with cells grown on a traditional cell culture substrate, in addition to cells grown on a variety of matrices.

Example 8

Non-Human Cells

Figure 7:
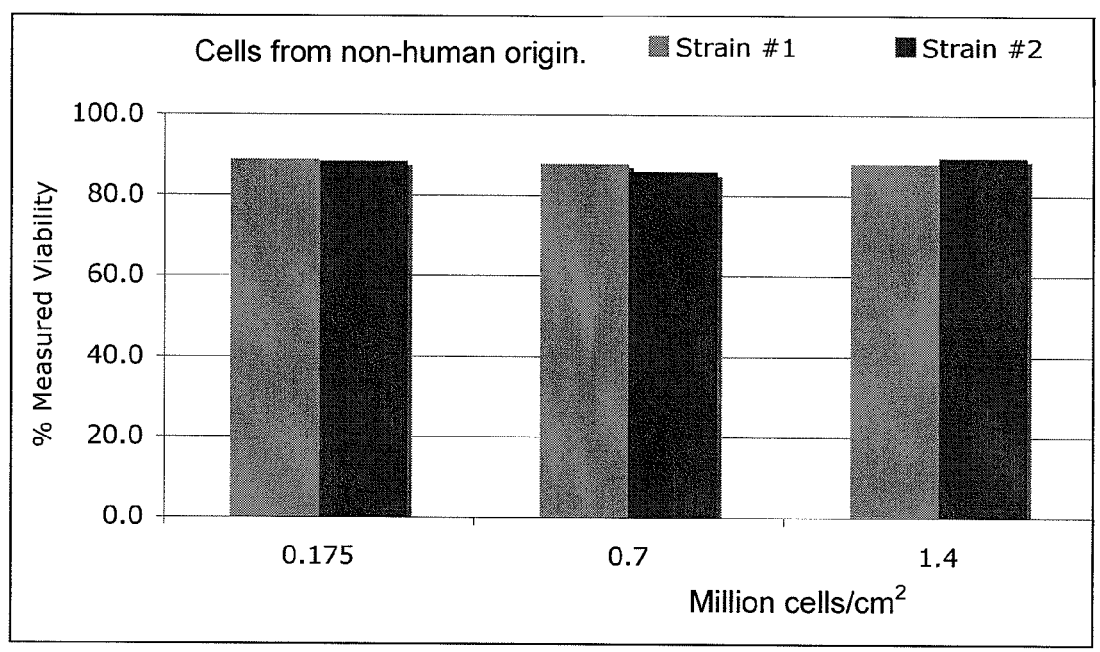
FIG. 7 is a graphical representation of an experiment which demonstrates that the accuracy of the disclosed assay is unaffected by the use of non-human cells.

To demonstrate the effectiveness of the assay on non-human cells, rabbit chondrocytes, from two donors, were seeded on ACI-MAIX® membrane matrix punches (6 mm in diameter) at densities ranging from 0.175 to $1.4 \times 10^6$ cells/cm². The cells were processed as in Example 1. The results are shown in FIG. 7 as the average viability of two replicates. The viability of strains 1 and 2, as determined by trypan blue exclusion just prior to seeding, were 88.0% and 84.9%, respectively. These results demonstrate that the assay performs well with cells from a non-human source.

Example 9

Alternative Substrate

Figure 8:
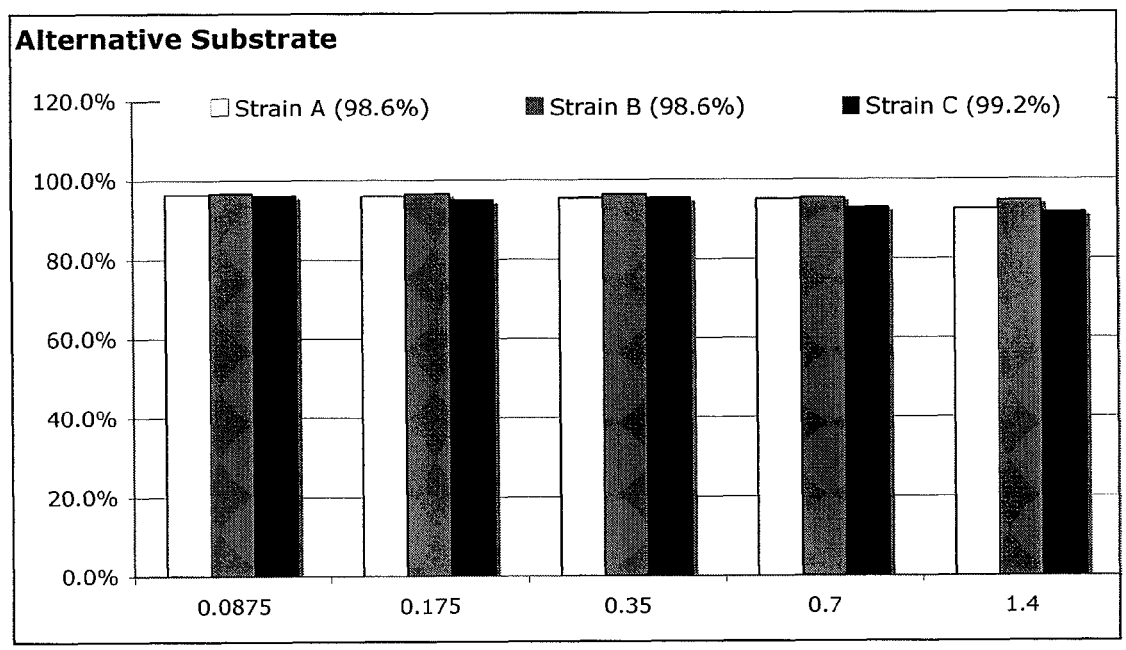
FIG. 8 is a graphical representation of an experiment which demonstrates that the disclosed assay can use substrates with leaving groups other than Rhodamine.

To demonstrate the effectiveness of the method using substrates other than the bis-(Ala-Ala-Phe)-Rhodamine-110, an alternative substrate, (Ala-Ala-Phe)-AMC (Bachem Cat No. 1-1415.0050, Torrance, Calif.), was tested using three strains of human chondrocyte seeding at densities in the range of $8.75 \times 10^4$ to $1.4 \times 10^6$ cells/cm². The cells were processed as in Example 1, except the bis-(Ala-AlaPhe)-Rhodamine-110 was replaced by (Ala-Ala-Phe)-AMC and the sample plate was read at excitation 360 nm-emission 440 nm. The viabilities for stain A, B, and C, determined by trypan blue exclusion prior to seeding, were 98.6%, 98.6%, and 99.2%, respectively. The results are shown in FIG. 8 as the average viability of two replicates. The result demonstrated that the alternative (Ala-Ala-Phe)-AMC substrate was effective (FIG. 8).

For all patent, application, or other reference cited herein, it should be understood that it is incorporated by reference in its entirety for all purposes as well as for the proposition that is recited. Where any conflict exits between a document incorporated by reference and the present application, this application will dominate.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of measuring the fraction of viable cells in a cell population maintained in a cell culture medium comprising:
   (a) detecting a cell death-stable enzyme activity in a portion of a cell culture conditioned medium not containing cells of the cell population;
   (b) detecting a cell death-stable enzyme activity in the cells and conditioned medium of a portion of the cell culture medium containing cells of the cell population; and
   (c) comparing the level of cell death-stable enzyme activity in the cells and conditioned medium portion of the cell culture medium containing cells to the level of cell death-stable enzyme activity in the portion of the cell culture conditioned medium not containing cells,
   wherein the cell death-stable enzyme activity is measured by the steps comprising:
   (i) contacting a sample with a substrate of the cell death-stable enzyme activity wherein the substrate is conjugated to a detectable leaving group; and
   (ii) detecting the leaving group,
   wherein the amount of leaving group detected is proportional to the level of cell death-stable enzyme activity,
   wherein the method additionally comprises adding an agent which attenuates the signal of the detectable leaving group,
   and wherein the fraction of viable cells in the cell population is directly proportional to the difference between the level of cell death-stable enzyme activity in the portion of the cell culture medium containing cells and conditioned medium and the level of cell death-stable enzyme activity in the portion of the cell culture conditioned medium not containing cells,
   wherein the agent which attenuates the signal of the leaving group is phenol red.

2. The method of claim 1, wherein a tissue-engineered product is maintained in the cell culture medium and:
   step (a) comprises detecting a cell death-stable enzyme activity in a portion of a cell culture conditioned medium not containing cells of the tissue-engineered product;
   step (b) comprises detecting a cell death-stable enzyme activity in the cells and conditioned medium of a portion of the cell culture medium containing cells of the tissue-engineered product; and
   step (c) comprises comparing the level of cell death-stable enzyme activity in the portion of the cell culture medium containing cells and conditioned medium of the tissue-engineered product to the level of cell death-stable enzyme activity in the portion of the cell culture conditioned medium not containing cells of the tissue-engineered product,
   wherein the tissue-engineered product comprises a three-dimensional scaffold or matrix and cells are present in the scaffold or matrix,
   and wherein the fraction of viable cells in the tissue-engineered product is directly proportional to the difference between the level of cell death-stable enzyme activity in the portion of the cell culture medium containing cells and conditioned medium of the tissue-engineered product and the level of cell death-stable enzyme activity in the portion of the cell culture conditioned medium not containing cells of the tissue-engineered product.

3. The method of claim 1, wherein the phenol red is present at a concentration of up to 500 mg/L.

4. The method of claim 1, wherein the cell death-stable enzyme activity is proteolytic.

5. The method of claim 4, wherein the cell death-stable enzyme activity comprises one or more tripeptidyl peptidases.

6. The method of claim 1, wherein the cell death-stable enzyme activity is both a necrotically and programmed cell death-stable enzyme activity.

7. The method of claim 1, wherein the cell death-stable enzyme activity is a programmed cell death-stable enzyme activity.

8. The method of claim 1, wherein the cell death-stable enzyme activity is a necrotically stable enzyme activity.

9. The method of claim 1, further comprising disrupting the membrane integrity of the tissue engineered product by shearing, sonication, low barometric pressure, high temperature, low temperature, chemical or enzymatic lysis, or membrane decoupling agents.

10. The method of claim 9, wherein the membrane integrity of the tissue engineered product is disrupted by the addition of an amphiphile.

11. The method of claim 10, wherein the amphiphile is saponin.

12. The method of claim 1, wherein the cells are mammalian.

13. The method of claim 12, wherein the cells are human.

14. The method of claim 13, wherein the cells are chondrocytes.

15. The method of claim 12, wherein the cells are grown on a matrix.

16. The method of claim 12, wherein the cells are present at a density of between $1.5 \times 10^4$ and $6 \times 10^6$ cells/cm$^2$.

17. The method of claim 1, wherein the cells are present at a high density of at least $2.0 \times 10^5$ cells/cm$^2$.

18. The method of claim 17, wherein the cells are present at between $2 \times 10^5$ and $6 \times 10^6$ cells/cm$^2$.

19. The method of claim 1, wherein the leaving group is chromogenic, luminogenic, or fluorescent.

20. The method of claim 19, wherein the leaving group is fluorescent.

21. The method of claim 20, wherein the leaving group is Rhodamine-110.

22. The method of claim 21 wherein the substrate is bis-(Ala-Ala-Phe)-Rhodamine-110.

23. The method of claim 20, wherein the leaving group is a coumarin derivative.

24. The method of claim 23, wherein the leaving group is AMC.

25. The method of claim 24, wherein the substrate is Ala-Ala-Phe-AMC.

\* \* \* \* \*